United States Patent [19]

Thompson

[11] 4,143,041

[45] Mar. 6, 1979

[54] 4'-DEOXYVINCRISTINE AND RELATED COMPOUNDS

[75] Inventor: Gerald L. Thompson, Indianapolis, Ind.

[73] Assignee: Eli Lilly and Company, Indianapolis, Ind.

[21] Appl. No.: 853,979

[22] Filed: Nov. 25, 1977

Related U.S. Application Data

[63] Continuation-in-part of Ser. No. 760,595, Jan. 19, 1977, abandoned.

[51] Int. Cl.$^2$ .................. C07D 519/04; A61K 31/475
[52] U.S. Cl. .................................... 260/244.4; 424/258
[58] Field of Search ...................................... 260/287 B

[56] References Cited

U.S. PATENT DOCUMENTS

| | | | |
|---|---|---|---|
| 3,392,173 | 7/1968 | Hargrove | 424/258 |
| 4,029,663 | 6/1977 | Gutowski et al. | 260/287 B |

FOREIGN PATENT DOCUMENTS 2558124  7/1976  France.

OTHER PUBLICATIONS

Kutney et al., Chem. Abst., vol. 83:28420z (1975).
Ibid, vol. 84:59829q (1975).
Ibid, vol. 85:160409y, Dec. 1, 1976.
Mason et al. ibid vol. 68:12879k
Neuss et al. ibid vol. 69:77565v 1968.

*Primary Examiner*—Raymond V. Rush
*Assistant Examiner*—David E. Wheeler
*Attorney, Agent, or Firm*—James L. Rowe; Arthur R. Whale

[57] ABSTRACT

4'-Deoxyvincristine, 4'-deoxy-1-formylleurosidine and the corresponding 4-desacetyl derivatives, useful in inhibiting the growth of experimental tumors.

10 Claims, No Drawings

4'-DEOXYVINCRISTINE AND RELATED COMPOUNDS

CROSS-REFERENCE

This application is a continuation-in-part of my co-pending application Ser. No. 760,595 filed Jan. 19, 1977, now abandoned.

BACKGROUND OF THE INVENTION

Several naturally-occurring alkaloids obtainable from Vinca rosea have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220), deoxy VLB "A" and "B", *Tetrahedron Letters*, 783 (1968) (desacetyl leurosine hydrazide is also disclosed therein); 4-desacetoxy vinblastine (U.S. Pat. No. 3,954,773); 4-desacetoxy-3'-hydroxyvinblastine (U.S. Pat. No. 3,944,554); leurocolombine (U.S. Pat. No. 3,890,325), leuroformine (N-formylleurosine, see Belgian Pat. No. 811,110) and vincadioline (U.S. Pat. No. 3,887,565). Two of these alkaloids, VLB and leurocristine, are now marketed as drugs for the treatment of malignancies in humans, particularly the leukemias and related diseases.

The dimeric indole-dihydroindole alkaloids obtainable from Vinca rosea can be represented by the formula:

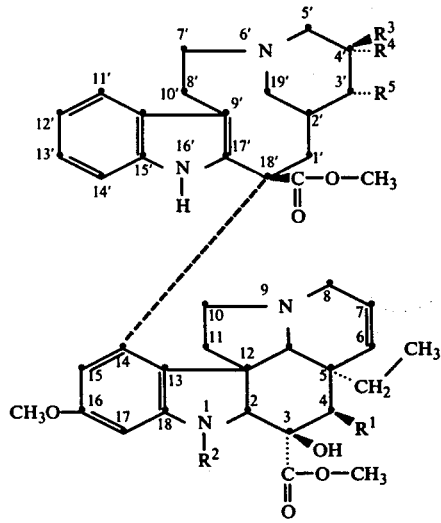

In the above formula where $R^1$ is acetoxy, $R^2$ is methyl, $R^3$ is hydroxyl, $R^4$ is ethyl and $R^5$ is H, VLB is represented; where $R^1$ is acetoxy, $R^2$ is formyl, $R^3$ is hydroxyl, $R^4$ is ethyl and $R^5$ is H, vincristine is represented; where $R^1$ is acetoxy, $R^2$ is methyl, $R^3$ is ethyl, $R^4$ is hydroxyl, and $R^5$ is H, leurosidine is represented; where $R^1$ is acetoxy, $R^2$ is methyl, $R^3$ and $R^5$ are H and $R^4$ is ethyl, deoxy VLB "A" is represented; where $R^1$, $R^2$ and $R^5$ are the same as in deoxy VLB "A" but $R^3$ is ethyl and $R^4$ is hydrogen, deoxy VLB "B" is represented; and where $R^1$ is acetoxy, $R^2$ is methyl, $R^3$ is ethyl and $R^4$ and $R^5$ taken together form an α-epoxide ring, leurosine is represented.

Of the above alkaloids, vincristine is the most useful, and the least available, from vinca. Recently, Jovanovics et al., U.S. Pat. No. 3,899,493, have developed an oxidative method for converting the relatively more abundant VLB into vincristine by chromic acid oxidation at low (−60° C.) temperatures. There are other relatively abundant alkaloids such as leurosine in the dimeric indole-dihydroindole fraction from vinca and it would be desirable to convert these directly or indirectly to vincristine or to a drug of comparable oncolytic activity. It is known that leurosine can be converted to deoxy VLB "B" (along with varying amounts of deoxy VLB "A") by treatment with Raney nickel in refluxing absolute ethanol—see Neuss, Gorman, Cone and Huckstep, *Tetrahedron Letters* 783-7 (1968). While leurosine demonstrated oncolytic activity in experimental tumors in mice, clinical response was limited. Deoxy VLB "A" and deoxy VLB "B" were reported to lack reproducible activity in experimental tumors in mice.

It is an object of this invention to convert leurosine via deoxy VLB "A" and "B" to oncolytically-active derivatives of deoxy VLB "A" and "B", thereby converting indirectly the relatively abundant alkaloid leurosine into a drug of greater potential clinical utility.

SUMMARY OF THE INVENTION

In fulfillment of the above and other objects, this invention provides compounds represented by the following formula:

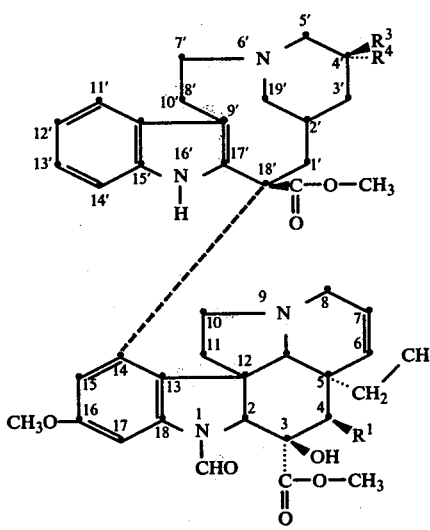

wherein $R^1$ is OH or acetoxy and one of $R^3$ and $R^4$ is hydrogen and the other is ethyl, and pharmaceutically-acceptable salts thereof formed with non-toxic acids. A compound according to the above formula in which $R^4$ is ethyl, $R^1$ is acetoxy and $R^3$ is hydrogen is named 4'-deoxyvincristine; a compound according to the above formula where $R^1$ is hydroxy but the other groups are the same is named 4'-deoxy-4-desacetylvincristine. Since the companion alkaloid to vincristine having a reverse configuration of hydrogen and ethyl at 4' from that found in vincristine is not known, those compounds in which $R^3$ is ethyl, and $R^4$ is hydrogen will be referred back to leurosidine which has the same configuration at 4' as deoxy VLB "B" and will be named as derivatives of 1-formylleurosidine; i.e., 4'-deoxy-1-formylleurosidine (or 4'-deoxyepivincristine) and 4'-deoxy-4-desacetyl-1-formylleurosidine where $R^1$ is acetoxy or hydroxy, respectively. In each of the above names, it will be understood that the 1-methyl group of leurosidine has been replaced by a formyl group and that the "1-desmethyl" term has been omitted to simplify the nomenclature.

Non-toxic acids useful for forming pharmaceutically-acceptable acid addition salts of the compounds of this invention include salts derived from inorganic acids such as: hydrochloric acid, nitric acid, phosphoric acid, sulfuric acid, hydrobromic acid, hydriodic acid, nitrous acid, phosphorus acid and the like, as well as salts of non-toxic organic acids including aliphatic mono and dicarboxylic acids, phenyl-substituted alkanoic acids hydroxy alkanoic and alkandioic acids, aromatic acids, aliphatic and aromatic sulfonic acids, etc. Such pharmaceutically-acceptable salts thus include the sulfate pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, naphthalene-1-sulfonate, naphthalene-2-sulfonate and the like salts.

The compounds of this invention according to Formula II above wherein $R^1$ is acetoxy are prepared by low temperature chromic acid oxidation of either deoxy VLB "A" or deoxy VLB "B". Compounds according to Formula II above wherein $R^1$ is hydroxy are prepared from the corresponding acetoxy compound by mild alkaline hydrolysis as with hydrazine hydrate or the like base.

Alternatively, 4'-deoxy VLB "A" and "B" can be converted to the corresponding 4-desacetyl derivatives by mild alkaline hydrolysis as above for the 1-formyl derivative. These 4-desacetyl derivatives can then be oxidized at low temperature ($-60°$ C.) with chromium trioxide without converting the 4-hydroxy group to a ketone to yield 4'-deoxy-4-desacetylvincristine and 4'-deoxy-4-desacetyl-1-formylleurosidine.

More specifically, the compounds of this invention can be prepared according to the following examples.

EXAMPLE 1

Preparation of 4'-Deoxyvincristine 582 mg. of chromium trioxide are dissolved in 5.8 ml. of acetic acid and 0.6 ml. of water. This oxidizing solution is added in dropwise fashion over a five-minute period to a stirred solution of 462 mg. of deoxy VLB "A" in 58 ml. of acetone and 2.9 ml. of acetic acid at a temperature of about $-50°$ C. The reaction mixture is stirred at this temperature for about 30 minutes and then cooled to $-65°$ C. at which temperature the reaction mixture is quenched with 12 ml. of 14 N aqueous ammonium hydroxide. The alkalinized reaction mixture is then poured onto 400 ml. of an ice-water mixture and the aqueous layer extracted with 150 ml. of ether followed by three extractions with 150 ml. of chloroform each. The organic layers are combined and the combined layers washed with dilute aqueous sodium bisulfite, separated and dried. Evaporation of the organic solvents leaves, as a residue, 4'-deoxyvincristine. Chromatography of the residue over 50 gm. of activity I silica is employed to further purify the desired compound. The chromatogram is developed as follows: 300 ml. of 3:1 ethyl acetate-methanol followed by 300 ml. of 1:1 ethyl acetate-methanol. After an initial 100 ml. fraction, 20 ml. fractions are collected. Fractions 8–20 are combined. Evaporation of the solvents from the combined fractions yields 279 mg. of a light tan solid which is substantially one spot (pure) material by thin-layer chromatography.

4'-Deoxyvincristine free base thus prepared has the following physical characteristics:

Infra-red spectrum; $\nu(CHCl_3)$ maxima at 3465, 1745, 1687 and 1220 cm$^{-1}$;

Ultraviolet spectrum; maxima at 210, 222, 255, 290 and 298 nm (nanometers);

100 MHz NMR, methyl singlets at $\delta 3.88$, 3.67 and 2.07.

mass spectrum: m/e 808(M$^+$), 806, 707.

4'-Deoxyvincristine, a tan solid, is dissolved in acetone and the acetone solution treated with 0.96 ml. of 0.36 M (2 percent volume/volume) sulfuric acid in absolute ethanol. A green solution results which is maintained at about 0° C. overnight. Crystallization is induced by scratching or seeding, and the solid crystalline 4'-deoxyvincristine sulfate is separated by filtration. The filter cake is washed with cold acetone. The sulfate salt is somewhat soluble in acetone so the filtrate is evaporated to dryness and the resulting residue recrystallized from ethanol. Crystalline 4'-deoxyvincristine sulfate thus obtained from ethanol was filtered and the filter cake washed with ethanol. Total yield of 4'-deoxyvincristine sulfate is 266 mg.

In similar fashion, 794 mg. of deoxy VLB "B" can be oxidized with 900 mg. of chromium trioxide in 10 ml. of glacial acetic acid and 1 ml. of water to yield 4'-deoxy-1-formylleurosidine. Thin-layer chromatography of the residue obtained directly from the oxidation mixture prior to purification indicates the presence of a major and a minor spot plus traces of other components. Recrystallization of the residue from anhydrous ethanol yields substantially one spot crystalline material which is isolated by filtration and the crystals washed with cold ethanol.

Chromatography of the crystalline free base thus obtained over 50 g. of silica using a 1:1 methylene dichloride-ethyl acetate solvent system containing 20, 30, 45 and 60 percent by volume of methanol as the eluant as follows:

| System | Quantity |
| --- | --- |
| 1:1 20% | 200 mls. |
| 1:1 30% | 100 mls. |
| 1:1 45% | 100 mls. |
| 1:1 60% | 400 mls. | yields the following fractions:

| Fraction | Volume of Eluate |
| --- | --- |
| 1 | 160 ml. |
| 2 | 100 ml. |
| 3 | 50 ml. |
| 4 | 50 ml. |
| 5 | 50 ml. |
| 6 | 120 ml. |
| 7 | 120 ml. |

Fractions 4–7 are combined to yield 597 mg. of a tan residue which in turn yields 435 mg. of white crystalline 4'-deoxy-1-formylleurosidine (from ethanol). The compound has the following physical characteristics:

Infra-red spectrum: $\nu(CHCl_3)$ 3470, 1743, 1690 and 1222 cm$^{-1}$;

Ultra-violet spectrum: maxima (EtOH) at 210, 222, 254, 290 and 298 nm;

100MHz NMR, methyl singlets at δ3.87, 3.65 and 2.07;

$pK_a'$ = 9.0 and 4.9 (66% DMF)

mass spectrum: m/e 808(M$^+$), 806, 777, 775, 336, 138.

The sulfate salt is prepared by dissolving 435 mg. of the free base in 10 ml. of hot ethanol and adding 1.5 ml. of 2 percent sulfuric acid in ethanol thereto. Crystalline 4'-deoxy-1-formylleurosidine sulfate deposits on cooling.

EXAMPLE 2

Preparation of 4'-Deoxy-4-desacetyl-1-formylleurosidine

About 744 mg. of 4'-deoxy-1-formylleurosidine are mixed with 10 ml. of anhydrous methanol and the mixture heated to refluxing temperature, at which temperature the compound dissolves to give a clear solution. 200 mg. of solid sodium carbonate are added and the reaction mixture is stirred for about 7.2 hrs. at which time TLC of the crude reaction components shows that virtually all starting 4'-deoxy-1-formylleurosidine has disappeared. The solvent is removed by evaporation and the residue containing 4'-deoxy-4-desacetyl-1-formylleurosidine formed in the above reaction is partitioned between water and methylene dichloride. The organic layer is separated and dried and the solvent is removed by evaporation yielding a white solid which is substantially pure 4'-deoxy-4-desacetyl-1-formylleurosidine.

The compound has the following physical characteristics:

mass spectrum: m/e 766(M$^{30}$), 764, 735, 254, 252, 205, 138 infrared spectrum: $\nu(CHCl_3)$ 3450, 1734, 1680, 1596, 1495, 1456, 1434 cm$^{-1}$;

100 MHz pmr spectrum: (CDCl$_3$) includes N-formyl at δ8.80, methyl singlets at 3.89 ($C_{16}$-OCH$_3$) and 3.66 ($C_{18'}$-CO$_2$CH$_3$), broadened multiplet at 3.82 ($C_3$-CO$_2$CH$_3$), and no N-CH$_3$ around 2.75 (or OCOCH$_3$ around 2.06).

The corresponding sulfate salt is formed as in the previous examples using acetone as a solvent with 0.26 ml. of 2% sulfuric acid in ethanol. Other solvents can be used and it is preferred to use a solvent in which the base is readily soluble but the sulfate salt substantially insoluble.

4'-Deoxy-4-desacetylvincristine and its sulfate salt are prepared in entirely analogous fashion from 4'-deoxyvincristine.

In carrying out the above hydrolysis reaction for preparing 4-desacetyl compounds, temperatures varying from ambient temperature (25° C.) to the boiling point of the particular solvent may be used. Other bases which can be employed include potassium t-butoxide, sodium or potassium methoxide or ethoxide, pyridine, triethylamine (or other tertiary amine), urea and the like in polar organic solvents such as the lower alkanols. Dilute sodium and potassium hydroxide can also be employed, in methanol for example, but precautions must be taken not to operate with base concentrations or reaction temperatures at which other hydrolysable groups in 4'-deoxyvincristine or 4'-deoxy-1-formylleurosidine are effected. Bases which operate only in non-polar solvents can also be used; i.e., sodium or lithium hydride in benzene, ether, THF, etc. or the sodium salt of dimethylsulfoxide in DMSO.

EXAMPLE 3

Alternate preparation of 4'-deoxy-4-desacetyl-1-formylleurosidine

A reaction mixture was prepared containing 1.48 g. of deoxy VLB "B", 1 g. of sodium carbonate and 100 ml. of methanol and was heated to reflux under a nitrogen atmosphere. Thin-layer chromatography of an aliquot taken at two hours indicated that the hydrolysis reaction to remove the 4-acetyl group was about half completed. The reaction mixture, after standing overnight at room temperature, was heated to reflux again for eight and one-half hours. Thin-layer chromatography of an aliquot using a 20:1:1:1 ether/diethylamine/toluene/methanol solvent indicated that the reaction had gone to completion. The solvent was removed from the reaction mixture by evaporation and the resulting residue was dissolved in a mixture of methylene dichloride and water. The methylene dichloride phase was separated and dried. Evaporation of the methylene dichloride yielded a residue comprising by TLC a very polar substance plus the expected 4'-deoxy-4-desacetylleurosidine. The residue which weighed 1.33 g. was dissolved in benzene. The highly polar material was substantially insoluble in benzene and was separated by filtration. The filtrate was evaporated to dryness and the residue weighing 500 mg. was chromatographed on Woelm silica gel using a 20:1:1 ether/diethylamine/toluene solvent system (with increasing quantities of methanol) as the eluant. The progress of the chromatography was followed by thin-layer chromatography and fractions shown to contain 4'-deoxy-4-desacetylleurosidine were combined and yielded 348 mg. of base on evaporation of the solvent. The residue was treated with 1.28 ml. of 2 percent sulfuric acid in methanol (0.36M) and the resulting solution was filtered to yield 315 mg. of 4'-deoxy-4-desacetylleurosidine sulfate.

4-Desacetyl-4'-deoxyleurosidine had the following physical characteristics:

Mass spectrum: m/e 752 (M$^+$), 750, 693, 691, 555, 338, 240, 138

Infrared spectrum: $\nu(CHCl_3)$ 3455, 1724, 1610, 1497, 1457, 1431 cm$^{-1}$.

100 MHz pmr spectrum: $\delta_{TMS}^{CDCl_3}$ 9.43 (br s, 1, $C_3$-OH), 7.92 (brs, 1, indole N-H), 7.47-7.63 (m, 1, $C_{11''}$-H), 7.06-7.31 (m, 3, $C_{12'-14''}$-H), 6.58 (s, 1, $C_{14}$-H), 6.10 (s, 1, $C_{17}$-H), 5.78-5.87 (m, 2, $C_{6,7}$-H), 4.10 (m, 1, $C_4$-H), 3.83 (s, 3, $C_{16}$-OCH$_3$), 3.78 (s, 3, $C_3$-CO$_2$CH$_3$), 3.70 (s, 1, $C_2$-H), 3.58 (s, 3, $C_{18''}$-CO$_2$CH$_3$), 2.75 (s, 3, N-CH$_3$), 0.76-1.06 (m, 6, $C_{21,21''}$-H).

834 mg. of 4'-deoxy-4-desacetylleurosidine obtained from filtrates and including solid filtered material were combined. The combined material probably contained 30-40 percent of the highly polar material referred to above. The combined material was dissolved in 100 ml. of acetone containing 7 ml. of acetic acid. The solution was stirred for 15 minutes at room temperature and then cooled to −65° C. in a dry-ice acetone bath under a nitrogen atmosphere. 1110 mg. of chromium trioxide were dissolved in 13 ml. of glacial acetic acid and 2 ml. of water. This solution was added in dropwise fashion to the solution of 4'-deoxy-4-desacetylleurosidine. The reaction mixture was stirred in the temperature range −60 to −65° C. for one hour and then quenched by the addition of 35 ml. of 14 M aqueous ammonium hydroxide. The reaction mixture was next poured onto ice and the resulting aqueous suspension extracted several times with chloroform. The chloroform extracts were combined, washed with water, and dried. Removal of the chloroform in vacuo yielded 794 mg. of a residue shown by thin-layer chromatography to contain essentially one-spot material in addition to a highly polar impurity present in the starting material. Chromatography of this residue over Woelm silica gel using a 20:1:1 ethylether/diethylamine/toluene solvent mixture containing 0.9 percent methanol was used as the initial eluant. 150 ml. portions of eluant were employed. The percent of methanol was increased for each successive 150 ml. eluant portion up to 15 percent. Fractions shown to contain 4'-deoxy-4-desacetyl-1-formylleurosidine by thin-layer chromatography were combined and yielded 293 mg. of pure 4'-deoxy-4-desacetyl-1-formylleurosidine after evaporation of the solvent. The sulfate salt was prepared as before.

4'-Deoxy-4-desacetylvincristine can be prepared as above by hydrolysing deoxy VLB "A" to yield 4'-deoxy-4-desacetyl VLB and then oxidizing this compound with $CrO_3$ in acetic acid at −60° C.

The compounds of this invention, as represented by Formula II above, particularly those in which $R^1$ is acetoxy, are powerful anti-tumor agents. In addition, an intermediate compound 4'-deoxy-4-desacetylleurosidine is also an oncolytic agent. In demonstrating the activity of these drugs against transplanted tumors in mice, a protocol was used which involved the administration of the drug by the intraperitoneal route at a given dose level for 7-10 days after innoculation with the tumor or alternatively, on the first, fifth, and ninth days after innoculation.

The following table — Table 1 — gives the results of several experiments in which transplanted tumors in mice were treated successfully with a compound of this invention.

In the table, column 1 gives the name of the compound; column 2, the transplanted tumor; column 3, the dose level or dose level range and the number of days the dosage was administered; column 4, the route of administration, and column 5, the percent inhibition of tumor growth or percent prolongation of survival time, e.g., B16. (ROS is an abbreviation of Ridgeway osteogenic sarcoma; GLS for Gardner lymphosarcoma; P1534(J) and L1210 are leukemias; CA755 is an adenocarcinoma; and B16 is a melanoma.).

TABLE I

| Compound | Tumor | mg./kg. × Days | Route | Percent Inhibition or Prolongation of Survival Time |
|---|---|---|---|---|
| 4'-Deoxy-1-desmethyl 1-formylleurosidine free base | B16 | 0.9 × 3 | IP | Toxic |
| | | 0.25–0.6 × 3 | " | 98–146 |
| | 755 | 0.6 × 3 | " | 54 |
| | | 0.4 × 3 | " | 73 |
| | | 0.25 × 3 | " | 47 |
| | | 0.2–0.3 × 10 | " | Toxic |
| | | 0.06–0.135 × 10 | " | 33–93 |
| | | 0.03–0.09 × 9 | " | 8–72 |
| | P1534(J) | 0.18 × 10 | " | Toxic |
| | P1534(J) | 0.08–0.18 × 10 | " | 9–46 |
| | GLS | 0.25–0.6 × 3 | " | 73–100 |
| 4'-Deoxy-1-desmethyl 1-formylleurosidine sulfate | GLS | 0.18 × 3 | " | 100 |
| | | 0.4 × 3 | " | 100 |
| | | 0.6 × 3 | " | Toxic |
| | | 0.25 × 3 | " | Toxic |
| | L1210 | 0.4–0.6 × 3 | " | Toxic |
| | | 0.25 × 3 | " | 65* |
| | ROS | 0.4 × 3 | " | 100 |
| | | 0.18 × 3 | " | 93 |
| | | 0.25 × 3 | " | Toxic |
| 4'-Deoxyvincristine sulfate | B16 | 0.30–0.9 × 3 | " | 36–143* |
| | 755 | 0.25–1.8 × 9–10 | " | Toxic |
| | | 0.06–0.13 × 9–10 | " | 15–100 |
| | | 0.9 × 3 | " | Toxic |
| | | 0.1–0.3 × 3 | " | 36–100 |
| | GLS | 0.4–0.6 × 3 | " | Toxic |
| | | 0.18–0.25 × 3 | " | 62–94 |
| 4'-Deoxy-4-desacetyl 1-desmethyl-1-formyl-leurosidine sulfate | B16 | 0.15–0.6 × 3 | " | 31–62** |
| | GLS | 0.6 × 3 | " | Toxic |
| | | 0.25–0.40 × 3 | " | 94–100 |
| | | 0.18 × 3 | " | 95 |
| 4'-deoxy-4-desacetyl-leurosidine sulfate | 755 | 0.6 × 3 | " | Toxic |
| | | 0.4 × 3 | " | 37 |
| | | 0.25 × 3 | " | 32 |
| | B16 | 0.6 × 3 | " | Toxic** |
| | | 0.3 × 3 | " | 103** |
| | | 0.15 × 3 | " | 77** |
| | GLS | 0.9 × 3 | " | Toxic |
| | | 0.6 × 3 | " | 63 |
| | | 0.4 × 3 | " | Toxic |

*1 or more indefinite survivors
**Delayed treatment-dosed 5th, 9th and 13th days In utilizing the novel compounds of this invention as anti-tumor agents, either the parenteral or oral route of administration may be employed. For oral dosage, a suitable quantity of a pharmaceutically-acceptable salt of a base according to Formula II formed with a non-toxic acid, such as the sulfate salt, is mixed with starch or other excipient and the mixture placed in telescoping gelatin capsules each containing from 7.5 to 50 mg. of active ingredients. Similarly, the anti-neoplastically active salt can be mixed with starch, a binder and a lubricant and the mixture compressed into tablets each containing from the 7.5–50 mgs. of salt. The tablets may be scored if lower or divided dosages are to be used. Parenteral administration is preferred however. For this purpose, isotonic solutions are employed containing 1-10 mg./ml. of a salt of an indoledihydroindole of Formula II such as the sulfate salt. The compounds are administered at the rate of from 0.01 to 1 mg/kg. and preferably from 0.1 to 1 mg./kg. of mammalian body weight once or twice a week or every two weeks depending on both the activity and the toxicity of the drug. An alternative method of arriving at a therapeutic dose is based on body-surface area with a dose in the range 0.1 to 10 mg./meter squared of mammalian body surface every 7 or 14 days being administered.

In utilizing a compound of this invention clinically, the clinical physician would administer the compound initially by the same route and in the same vehicle and probably against the same types of tumors as are indicated for vincristine or VLB. The dose levels employed would reflect the difference in dose levels found in the treatment of experimental tumors in mice, the dose levels of the compounds of this invention being less than those used with vincristine and VLB. In clinical tests, as with other anti-tumor agents, particular attention would be paid to the effect of the oncolytic compounds of this invention against the ten "signal" tumors set forth at page 266 of "The Design of Clinical Trials in Cancer Therapy" edited by Staquet (Futura Publishing Company, 1973).

I claim:

1. A compound of the formula

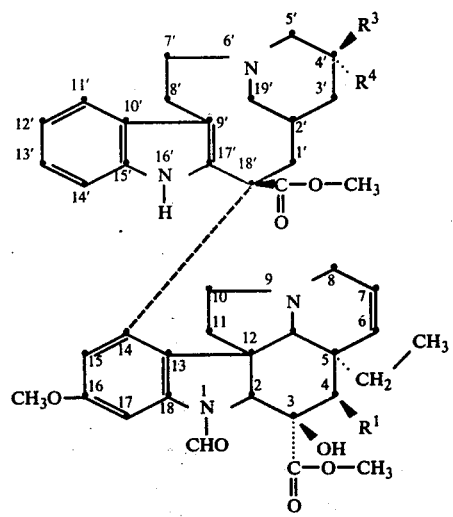

wherein $R^1$ is OH or acetoxy and one of $R^3$ and $R^4$ is hydrogen and the other is ethyl, and pharmaceutically-acceptable salts thereof formed with non-toxic acids.

2. A compound according to claim 1 in which $R^1$ is acetoxy.

3. A sulfate salt of a compound according to claim 2.

4. A compound according to claim 1 in which $R^1$ is acetoxy, $R^3$ is hydrogen and $R^4$ is ethyl, said compound being 4'-deoxyvincristine.

5. A sulfate salt of a compound according to claim 4, said salt being 4'-deoxyvincristine sulfate.

6. A compound according to claim 1 in which $R^1$ is acetoxy, $R^3$ is ethyl and $R^4$ is hydrogen, said compound being 4'-deoxy-1-formylleurosidine.

7. A sulfate salt of a compound according to claim 6, said salt being 4'-deoxy-1-formylleurosidine sulfate.

8. A compound according to claim 1 in which $R^1$ is hydroxyl, $R^4$ is hydrogen and $R^3$ is ethyl, said compound being 4'-deoxy-4-desacetyl-1-formylleurosidine.

9. A compound of the formula

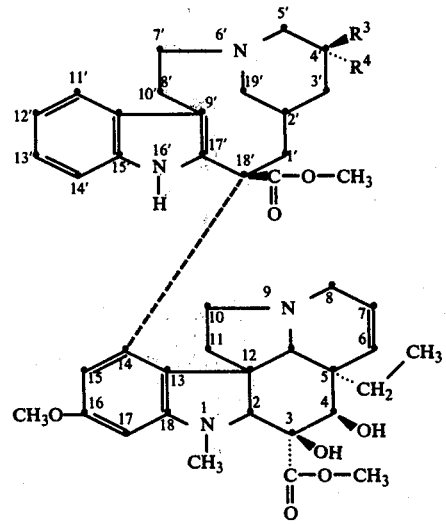

wherein one of $R^3$ and $R^4$ is hydrogen and the other is ethyl.

10. A compound according to claim 9 wherein $R^3$ is ethyl and $R^4$ is H, said compound being 4-desacetyl-4'-deoxyleurosidine.

* * * * *